(12) United States Patent
Korichi et al.

(10) Patent No.: US 9,064,180 B2
(45) Date of Patent: Jun. 23, 2015

(54) METHOD FOR CHARACTERIZING THE TONE OF THE SKIN AND INTEGUMENTS

(75) Inventors: Rodolphe Korichi, Saint Jean le Blanc (FR); Sandrine Stephan, Beaugency (FR)

(73) Assignee: LVMH RECHERCHE, Saint Jean de Braye (FR)

(*) Notice: Subject to any disclaimer, the term of this patent is extended or adjusted under 35 U.S.C. 154(b) by 429 days.

(21) Appl. No.: 13/474,218

(22) Filed: May 17, 2012

(65) Prior Publication Data

US 2012/0300050 A1 Nov. 29, 2012

(30) Foreign Application Priority Data

May 27, 2011 (FR) .................................... 11 54674

(51) Int. Cl.
*H04N 7/18* (2006.01)
*G06K 9/46* (2006.01)
(Continued)

(52) U.S. Cl.
CPC ............ *G06K 9/4652* (2013.01); *A61B 5/0059* (2013.01); *A61B 5/441* (2013.01); *G06T 7/408* (2013.01); *G01J 3/513* (2013.01); *G01J 3/462* (2013.01); *G01J 3/463* (2013.01);
(Continued)

(58) Field of Classification Search
CPC ....... A61B 5/0059; A61B 5/441; G01J 3/462; G01J 3/463; G01J 3/513; G06K 9/4652; G06T 2207/10024; G06T 2207/30088; G06T 7/408
USPC .......................................................... 348/77
See application file for complete search history.

(56) References Cited

U.S. PATENT DOCUMENTS 4,894,547 A * 1/1990 Leffell et al. ............... 250/461.2
6,148,092 A * 11/2000 Qian ............................. 382/118
(Continued)

OTHER PUBLICATIONS

Kanzawa et al, Human Skin Detection by Visible and Near-Infrared Imaging, Jun. 2011.*
(Continued)

*Primary Examiner* — Shan Elahi
(74) *Attorney, Agent, or Firm* — Hamre, Schumann, Mueller & Larson, P.C.

(57) ABSTRACT

The invention relates to a method and apparatus for characterizing the tone of the skin or integuments.
The apparatus comprises a digital camera or a digital photographic apparatus (12) allowing the capture of at least one digital image (14) of at least one determined skin zone (34, 36, 38, 40), said image being defined by a multiplicity of pixels (N) that is transmitted to a digital image processing device comprising means for splitting the digital image into three color planes: red, green, blue, termed R, G, B;
 c) means for extracting each of these planes R, G, B; and on each plane, calculation means for logging the grey level value for each of the pixels, i.e. N values, which are optionally processed mathematically by appropriate calculation means, so as to obtain at least one graphical or statistical value and/or at least one value characteristic of the grey levels for each plane, corresponding to a value characteristic of the color of the skin; as well as the luminosity value L; and
 d) means for characterizing the tone of the skin or integuments on the basis of the combination of the value characteristic of the color of the skin or integuments and of the Luminosity value L.
The invention finds an industrial application in a method for assessing the whitening effect of a cosmetic product.

23 Claims, 3 Drawing Sheets

(51) Int. Cl.
*A61B 5/00* (2006.01)
*G06T 7/40* (2006.01)
*G01J 3/51* (2006.01)
*G01J 3/46* (2006.01)

(52) U.S. Cl.
CPC ............... *G06T2207/10024* (2013.01); *G06T 2207/30088* (2013.01)

(56) References Cited

U.S. PATENT DOCUMENTS

| | | | |
|---|---|---|---|
| 7,515,747 B2* | 4/2009 | Okutomi et al. | 382/167 |
| 7,794,084 B2* | 9/2010 | Masaki et al. | 351/206 |
| 2005/0118121 A1* | 6/2005 | Kuroda | 424/63 |
| 2006/0149151 A1* | 7/2006 | Ladjevardi et al. | 600/475 |
| 2007/0040907 A1* | 2/2007 | Kern et al. | 348/77 |
| 2007/0058858 A1 | 3/2007 | Harville et al. | |
| 2007/0091091 A1* | 4/2007 | Gardiner et al. | 345/440 |
| 2007/0229658 A1* | 10/2007 | Kanamori et al. | 348/135 |
| 2008/0080766 A1 | 4/2008 | Payonk et al. | |
| 2008/0107361 A1* | 5/2008 | Asukai et al. | 382/317 |
| 2010/0085538 A1* | 4/2010 | Masaki et al. | 351/206 |
| 2010/0185064 A1 | 7/2010 | Bandic et al. | |

OTHER PUBLICATIONS

Pladellorens, A device for the color measurment and detection of spots on the skin, 2008.*
Pladellorens et al "A device for the color measurement and detection of spots on the skin". SKIN RESEARCH AND TECHNOLOGY, vol. 14, No. 1, Jan. 1, 2007, (pp. 65-70), XP55020236.

* cited by examiner

METHOD FOR CHARACTERIZING THE TONE OF THE SKIN AND INTEGUMENTS

The invention relates to a method for characterizing the tone of the skin or integuments and its implementation in a method for evaluating the cosmetic efficacy of a cosmetic composition as regards care or make-up.

PRIOR ART

The skin colour of an individual results mainly from genetic predispositions related in particular to the secretion of melanins by the melanocytes. It is, however, tinged by numerous factors such as exposure to the sun, the fineness of the epidermis revealing to a greater or lesser extent the blood micro-circulation, diet, the incidence of pathologies or else the taking of medicine.

The visual perception of this colour by an observer is also influenced by the way in which the skin scatters the light, which may be influenced by the state of hydration or the presence of pollutants, inducing a lustre which may vary under the influence of one of its factors.

It is possible in this way to distinguish the "skin colour", which may be reduced with the aid of numerical tools to a combination of primary colours, and the "tone of the skin", a more subjective notion which represents the visual perception resulting from the colour of the skin and its lustre.

It is therefore important to be able to employ tools and methods of characterization which make it possible to study the tone of the skin or integuments.

Procedures for studying the skin calling upon computerized tools are known.

A procedure and a device for the non-invasive estimation of a relative age of a person, based on a so-called NIR near infrared procedure using a wavelength in the region of 700 to 2500 nanometers, is known from document U.S. Pat. No. 6,551,982 B1.

Imaging systems and procedures for analysing the skin implementing the acquisition and the creation of diverse digital images with the purpose of visualizing skin defects, and thereafter the consideration of a sub-image containing the skin defect, are further known from document WO 00/67398 A1.

A colour digital image analysis method and apparatus, comprising different embodiments depending on whether it entails evaluating the colour of the skin in particular so as to evaluate pigmentary blemishes, or pores, on the one hand, and on the other hand for the evaluation of wrinkles, are further known from document US 2004/0218810 published on 4 Nov. 2004.

For the evaluation of the colour of the skin, there are thus envisaged a dedicated module referenced 320, FIG. 3, and diverse steps shown in FIGS. 6 to 10 which carry out image captures in the plane portions of zones of the skin of the face, such as the brow F, the cheeks C, illuminated by white light and with a digital apparatus [0007], and disposed at a fixed distance [0009]. The description specifies in paragraphs [0052] to [0060] the extraction of signals R (red), G (green), B (blue) (445 in FIG. 4) which are converted, in each image capture zone, into signals H ("HUE" or tone), S (saturation), V (value), see definitions [0035].

The module 320 can create a histogram on the basis of each HSV signal, as shown in FIG. 10A, by counting the number of pixels having each graduation of H, S and V (470, FIG. 4). Each Histogram on the screen 155 of FIG. 10A shows the results of the past and current examinations. The operator can thus confirm the effect of a whitening cosmetic product on the skin, see [0054].

Finally, a method and an apparatus for capturing digital colour images of skin zone(s) of a person, implementing image analysis software, that can be chosen from among public domain software, so as to determine certain characteristics of the skin, such as colour or discoloration, oiliness, texture, wrinkles or lines, and pores, are known from the document KERN US 2007/0040907 (see §43 to 48). These characteristics are thereafter used to advise people about the care products to be used. In practice, this document relates especially to a particular structure of digital image capture device (see FIGS. 1 to 14).

A method and device for improving the texture of the skin implementing a method and device for image analysis, comprising the generation of a digital image and the detection of troughs and peaks in the image so as to detect the skin characteristics which are thereafter processed by processing software to improve the quality of the image, are further known from U.S. Pat. No. 7,082,211 V1. FIG. 5C shows a colour classifier. (col 10, lines 31 to 45).

The article of PLADELLORENS et al in SKIN RESEARCH AND TECHNOLOGY, Vol 14, No 11 january 2007, pages 65-70, XP55020236 focuses on the measure of the Luminosity L from the colour image and uses a spectrophotometer.

In conclusion, the prior art does not give any genuine procedure and apparatus for determining the tone of the skin or integuments based on the colour and luminosity parameters on the basis of the initial digital images and still less relating to their application in order to objectively evaluate the efficacy of a cosmetic composition as regards care or make-up of the skin or integuments, in contradistinction to the invention described hereinafter.

PURPOSES OF THE INVENTION

The purpose of the present invention is to solve the technical problem consisting of the provision of a novel method and of a novel apparatus for determining the tone of the skin or integuments that are relatively easy to implement, dependable and reliable as regards the result obtained, in an objective manner.

The purpose of the present invention is also to solve the technical problem consisting of the provision of a novel method and of a novel apparatus for determining the tone of the skin or integuments on the basis of colour digital images and with the minimum of steps of processing of the digital images obtained, by virtue of a system for processing digital images comprising simple software that may even be available commercially.

The purpose of the present invention is further to solve the technical problem consisting of the provision of a method for evaluating the cosmetic efficacy of a cosmetic product implementing the method or the apparatus for determining the tone of the skin or integuments.

The present invention affords a satisfactory solution to these two technical problems.

DETAILED DESCRIPTION OF THE INVENTION

Definitions

The expression "tone of the skin or integuments" is intended to mean the visual perception of the skin or integuments of an individual, resulting both from the coloration or colour of the skin or integuments, and the luminosity or lustre thereof.

The expression "coloration or colour of the skin or integuments" is intended to mean the overall colour ensuing from the analysis of a digital image of said skin or integuments, and obtained by the combination of its colour components, namely the colour Red, denoted R; the colour Green, denoted G; and the colour Blue, denoted B.

The expression "the luminosity" is intended to mean the luminosity value L such as obtained by the procedure for transforming R, G, B values to the CIE L a*b* benchmark for a D65 illuminant and an observer at 10 degrees.

According to a first aspect, the present invention provides a method for determining the tone of the skin or integuments of a person, characterized in that it comprises the following steps:
the capture of a digital colour image of at least one zone of the skin or integuments, said image comprising a number N of pixels;
the extraction of the three colour planes Red (R), Green (G), and Blue (B) of this colour digital image;
the evaluation of the colour of the skin or integuments on the basis of the value of the grey level of each pixel from at least some of the N pixels of the image for at least two planes, in particular for the three planes, R, G, B;
the evaluation of the Luminosity L on the basis of the value of the grey level for each pixel from at least some of the N pixels of the image for at least two planes, in particular for the three planes, R, G, B; and
the characterization of the tone of the skin or integuments ensuing from said evaluation of the colour of the skin or integuments and of said evaluation of the luminosity L.

According to a particular embodiment of this method, the latter is characterized in that it comprises the following steps:
a) at least one digital colour image of at least one determined zone of skin or of integuments is captured, said digital colour image being defined by a multiplicity (N) of pixels, with the aid of a digital camera or a digital photographic apparatus, that is transmitted to a device for processing digital images which records it;
b) the digital colour image thus recorded is split into three colour planes: red (R), green (G), blue (B), termed R, G, B, with the aid of said image processing device;
c) each of these planes R, G, B is extracted; and on each plane the grey level value is logged for each of the pixels, i.e. N values, which are optionally processed mathematically by appropriate calculation means, so as to obtain at least one graphical or statistical value and/or at least one value characteristic of the grey levels for each plane R, G, B, corresponding to a value characterizing the colour of the skin; as well as to obtain a luminosity value L;
d) the tone of the skin or integuments is characterized on the basis of the combination of the value characteristic of the colour of the skin or integuments and of the Luminosity value L.

According to a particular variant embodiment, the method is characterized in that an image zone representative of the tone to be observed is chosen and on at least one part of this zone, a parametrization of at least one parameter is carried out, chosen from among the mean grey level of the image, the aggregate area of the grey levels, and the variance; as well as the luminosity L.

According to another particular embodiment of this method, the latter is characterized in that a histogram of each digital image is plotted in the form of a curve in a plane, and for which for example the vertical axis represents the number of pixels or the proportion of pixels in the image for each colour plane R, G, and B and the horizontal axis represents the set of values of grey levels of the image, or vice versa; thereby obtaining a histogram R, a histogram G, and a histogram B.

According to a further particular embodiment of this method, the latter is characterized in that the colour of the skin or integuments is determined by calculating the tightness, denoted ($\Delta_{RGB}$), either of the histograms R, G, B furthest apart, or of at least two of said histograms R, G, B.

According to another particular embodiment of this method, the latter is characterized in that the more or less desaturated character of the colour is determined with the aid of at least one of the following parameters:
either the area of overlap of at least two histograms, preferably of the three histograms R, G and B,
or the number of pixels for which a single grey level value is logged for the three planes R, G and B,
or the arithmetic mean and optionally the deviation from the mean, of the grey levels logged for the three planes R, G and B,
or their combinations.

According to yet another particular embodiment of this method, the latter is characterized in that a whiteness index ($I_w$) of the skin is calculated according to the formula:

$$(I_w) = \mathrm{Arc\ tn}(L/(\Delta_{RGB}))$$

According to another particular embodiment of this method, the latter is characterized in that said method is reproduced on various zones of skin or integuments of the same individual, in particular on various skin zones of the face.

According to a further particular embodiment of this method, the latter is characterized in that a value for the luminosity L, the index ($\Delta_{RGB}$) and the index ($I_w$) is calculated for each zone.

According to a particular embodiment of this method, the latter is characterized in that at least one skin zone exhibits a pigmentation defect such as pigmentary blemish, and that at least one other "control" skin zone is normally pigmented.

According to a particular embodiment of this method, the latter is characterized in that the image capture of at least one zone of the skin or integuments is carried out under illumination with white light.

According to another particular embodiment of this method, it is possible to carry out a thresholding of the grey levels, that is to say it is possible to eliminate the grey levels below a certain predetermined grey level threshold, so as to eliminate spurious elements.

According to yet another particular embodiment of this method, it is possible to choose a limited area of skin or of the integuments to be analysed, on the whole of which it is possible to undertake the characterization.

According to a particular variant embodiment, said limited area can represent an area of about 1 cm$^2$ to 10 cm$^2$.

According to a particular characteristic of the method on the invention, it is possible to perform an enlargement of said digital image obtained by the camera or the photographic apparatus allowing an operator to better visualize the zone studied and optionally to evaluate the thresholding of the grey levels, making it possible to eliminate spurious elements or artefacts.

According to an advantageous embodiment of the method according to the invention, said method is characterized in that a digital colour camera of TRI-CCD type or a colour digital photographic apparatus is used. A digital colour camera such as this is available commercially in particular from the company SONY, and a digital photographic apparatus such as this, for example of D70S type, is available commercially from the company NIKON. It is also possible to use the VISIA-CR system from the co. Canfield, for the acquisition of the colour digital images. The acquisitions may be performed advantageously on ¾ faces, in standard white light.

According to a particular embodiment of the method on the invention, said method is characterized in that at least one image or a plurality of images of the skin of one and the same person, in particular on several different zones, is recorded on a device for recording digital data.

According to a particular variant embodiment, said image capture zone corresponds to any cutaneous zone representative of the face, of the body or of the integuments. Advantageously, this will entail a zone chosen from among the group consisting of a median zone of the brow, and/or of a zone of the cheek and/or of the nails.

According to a second aspect, the present invention provides an apparatus for characterizing the tone of the skin or integuments of a person, characterized in that it comprises:
  a) a digital camera or a digital photographic apparatus allowing the capture of at least one digital image of at least one determined zone of skin or integuments, said digital image being defined by a multiplicity of pixels (N) that is transmitted to a digital image processing device;
  b) means for splitting the digital image into three colour planes: red, green, blue, termed R, G, B, with the aid of said image processing device;
  c) means for extracting each of these planes R, G, B; and on each plane, calculation means for logging the grey level value for each of the pixels, i.e. N values, which are optionally processed mathematically by appropriate calculation means, so as to obtain at least one graphical or statistical value and/or at least one value characteristic of the grey levels for each plane, corresponding to a value characterizing the colour of the skin; as well as to obtain a luminosity value L;
  d) means for characterizing the tone of the skin or integuments on the basis of the combination of the value characteristic of the colour of the skin or integuments and of the Luminosity value L.

According to a particular embodiment, this apparatus is characterized in that, on an image zone representative of the tone to be observed and on at least one part of this zone, the calculation means carry out a parametrization of at least one parameter chosen from among the mean grey level of the image, the aggregate area of the grey levels, and the variance or their combinations.

According to a particular embodiment, this apparatus is characterized in that the calculation means plot a histogram of each digital image in the form of a curve in a plane, and for which for example the vertical axis represents the number of pixels or the proportion of pixels in the image for each colour plane R, G, and B and the horizontal axis represents the set of the grey levels of the pixels of the image, thereby obtaining a histogram R, a histogram G, and a histogram B.

According to a particular embodiment, this apparatus is characterized in that the desaturation of the colour of the skin or integuments is determined by calculating the tightness, denoted ($\Delta_{RGB}$), either of the histograms R, G, B furthest apart, or of at least two of said histograms R, G, B.

According to another particular embodiment, this apparatus is further characterized in that the more or less saturated/desaturated character of the colour is determined by calculating at least one of the following parameters:
  either the area of overlap of at least two histograms, preferably of the three histograms R, G, B,
  or the number of pixels for which a single grey level value is logged for the three planes R, G and B.
  or the arithmetic mean and optionally the deviation from the mean, of the grey levels logged for the three planes, or their combinations.

According to yet another particular embodiment, this apparatus is characterized in that a whiteness index ($I_w$) of the skin is calculated according to the formula:

$$(I_w) = \text{Arc tn}(L/\Delta_{RGB})$$

According to a particular embodiment, this apparatus is characterized in that the calculation means calculate for each zone a value for the luminosity L, the index ($\Delta_{RGB}$) and the index ($I_w$), in particular for several selected zones of the skin or integuments.

According to a further particular embodiment, this apparatus is further characterized in that it furthermore comprises a device for illumination with white light allowing the capture of at least one image of at least one zone of the skin under such illumination.

According to another particular embodiment, a digital colour camera of TRI-CCD type available commercially in particular from the company SONY or a digital photographic apparatus of D70S type available commercially from the company NIKON is envisaged. It is also possible to use the VISIA-CR system from the Company Canfield for the acquisition of the images. These acquisitions may be performed on at least one zone of at least one cheek on faces positioned at ¾, with standard white light.

According to yet another particular embodiment, this apparatus comprises a computer combined with a monitor comprising a screen, a keyboard and a mouse and comprising software integrating all of the abovementioned means including:
  the means for splitting the digital image into three colour planes: red, green, blue, termed R, G, B;
  the means for extracting each of these planes R, G, B;
  the appropriate means of mathematical calculation; and
  the means for recording at least one image or a plurality of images of the skin or integuments.

According to a particular embodiment, the calculation means take into account the mean of each parameter obtained on the various images obtained respectively with the various zones of the skin or integuments considered, so as to obtain each global mean parameter which is advantageously recorded and can, according to a variant embodiment, be used, for each person, to construct a curve for calibrating the tone of the skin.

According to a particular embodiment, the apparatus comprises means for recording at least one image or a plurality of images of the skin or integuments of one and the same person, in particular on several zones, in particular of at least one cheek.

According to a third aspect, the present invention further relates to a method for evaluating the cosmetic efficacy of a cosmetic composition as regards care or make-up on at least one person having need thereof, characterized in that:
  a) at least one first colour digital image is captured before application of said cosmetic product to at least one determined zone of skin or integuments;
  b) said first digital colour image is decomposed into three colour planes red (R), green (G) and blue (B) so as to determine the colour of the skin or integuments, as well as to determine the value of the luminosity L, as reference parameters of colour and luminosity L of the skin or integuments before treatment;

c) the care or make-up is undertaken, comprising one or more applications of said cosmetic composition to said at least one zone of skin or integuments over a predetermined time period;

d) at least one second digital image of said at least one zone of skin or integuments is captured, after said predetermined time period, and the current parameters of colour and luminosity L after treatment are determined as indicated under b), on said second image;

e) the current parameters of colour and luminosity L of the second image obtained after treatment are compared with the reference parameters of colour and luminosity L of the first image before treatment; and f) the efficacy or the absence of efficacy of said cosmetic composition is concluded as a function of the obtaining or of the non-obtaining of current parameters of colour and luminosity L that are significantly different from the reference parameters of colour and luminosity L.

According to a particular embodiment, the method is characterized in that the colour parameter is determined on each digital image decomposed into three planes respectively of colour Red, R; of colour Green, G; and colour Blue, B, termed R, G, B planes.

According to another particular embodiment, the method is characterized in that a histogram of each digital image is plotted in a plane, and for which for example the vertical axis represents the number of pixels or the proportion of pixels in the image for each colour plane R, G, and B and the horizontal axis represents the set of values of grey levels of the pixels of the image, so as to obtain a histogram R, a histogram G, and a histogram B.

According to another particular embodiment, the method is characterized in that the more or less desaturated character of the mean colour is determined by calculating the level of overlap of at least two histograms, preferably of the three histograms R, G, B.

According to another particular embodiment, the method is characterized in that the efficacy of the cosmetic composition is determined by calculating the tightness, denoted ($\Delta_{RGB}$), either of the histograms R, G, B furthest apart, or of at least two of said histograms R, G, B.

According to a further particular embodiment, the method is characterized in that a whiteness index ($I_w$) of the skin is calculated according to the formula:

$$(I_w) = \text{Arc tn}(L/\Delta_{RGB}))$$

According to another particular embodiment, the method is characterized in that said method is reproduced on various zones of skin or integuments of the same individual.

According to another particular embodiment, the method is characterized in that a value for the luminosity L, the index ($\Delta_{RGB}$) and the index ($I_w$) is calculated for each zone.

According to yet another particular embodiment, the method is characterized in that at least one skin zone exhibits a pigmentation defect such as pigmentary blemish, and that at least one other "control" skin zone is normally pigmented.

According to another particular embodiment, the method is characterized in that a whitening care is carried out on at least said zone of skin or integuments, and a cosmetic whitening composition is applied during said predetermined time period, so as to conclude as to the efficacy, or the absence of efficacy, of said cosmetic composition as a function of the obtaining, or of the non-obtaining, of current parameters of colour and luminosity L that are significantly different from the reference parameters of colour and luminosity L; and in particular the whiteness index is calculated and the efficacy, or the non-efficacy, of the cosmetic composition is concluded depending on whether the trend in the whiteness index is or is not significantly positive.

According to yet another particular embodiment, the method is characterized in that a tanning care is carried out on at least said zone of skin or integuments, and a cosmetic tanning composition is applied, during said predetermined time period, so as to conclude as to the efficacy, or the absence of efficacy, of tanning, of said cosmetic composition as a function of the obtaining, or of the non-obtaining, of current parameters of colour and luminosity L that are significantly different from the reference parameters of colour and luminosity L.

According to an advantageous embodiment of this method, the latter is characterized in that the significant decrease is obtained with a probability of error of less than or equal to 5%.

By virtue of the methods and of the apparatus according to the invention, the previously stated technical problems are solved in a simple, dependable and reliable manner.

Other purposes, characteristics and advantages of the invention will be clearly apparent in the light of the explanatory description which follows, given with reference to a currently preferred embodiment of the invention.

DESCRIPTION OF THE FIGURES

In the figures.

It will thus be observed that a whitening product will be considered to be efficacious if the trend in the whiteness angle Arc tn (L: ΔRGB) between two points is positive.

It is observed that when the individual typological angle ITA lies between 0 and 10°, the skin is of brownish tone; when this angle lies between 10 and 28°, the skin exhibits a tanned tone or pigmentation; when this angle lies between 28 and 41°, the skin exhibits an intermediate tone; when the angle lies between 41 and 55°, the skin is fair; when the angle is greater than 55°, the skin is very fair.

EXAMPLE 1

Figure 1:
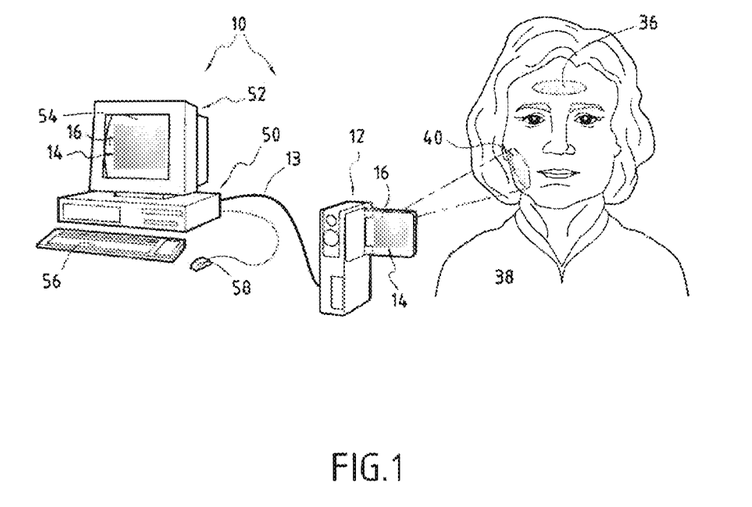
FIG. 1 represents an apparatus for characterizing the tone of the skin of a person, or integuments, making it possible to implement the previously described method for characterizing the tone of the skin or integuments and the method for evaluating the cosmetic efficacy of a cosmetic composition as regards care or make-up on at least one person having need thereof with here, in a first embodiment, the capture of images for example of at least one determined skin zone such as particularly the brow, the cheeks, and for which the tone must be particularly analysed.

Description of the Apparatus Represented in FIG. 1

With reference to the figures, and in particular with reference to FIG. 1, there has been represented a currently preferred embodiment of an appliance according to the invention, represented by the general reference number 10.

This apparatus 10 is designed to carry out the characterization of the tone of the skin or integuments of a person, and is characterized in that it comprises:

a) a digital camera or digital photographic apparatus 12 allowing the capture of at least one digital image 14, of at least one determined skin zone 36, 40, said image being defined by a multiplicity (N) of pixels that is transmitted to a digital image processing device.

For the needs of this image capture, the determined zones of the skin are illuminated by an illumination device, not represented, with white light or with ultraviolet light.

According to a particular embodiment of the apparatus according to the invention, a digital colour camera 12 of TRI-CCD type, such a colour camera being available commercially in particular from the company SONY or a digital photographic apparatus of D70S type available commercially from the company NIKON is envisaged. In this example the VISIA-CR system from the Company Canfield will be used for the acquisition of the images. These acquisitions may be performed on at least one zone of at least one cheek on faces positioned at ¾, as represented in FIG. 1; and with standard white light.

According to a particular variant embodiment, said camera or said photographic apparatus 12 makes it possible to capture an image of an area of the skin having about 1 cm² to 10 cm².

Also, as is well known to the person skilled in the art, such a device for processing digital images is available commercially for example in the form of software, that can be integrated into a computer 50 linked to said camera 12 by an appropriate cord 13. Said computer 50 is naturally combined with a monitor 52 together with its screen 54 and its keyboard 56 and a mouse 58.

b) the device for processing digital images comprises means for splitting the digital image into three colour planes: red, green, blue, termed R, G, B, c) the device for processing digital images also comprises means for extracting each of these planes R, G, B;

d) means for calculation on each plane, here envisaged in said software, for logging the grey level value for each of the pixels, i.e. N values, which are optionally processed mathematically by appropriate calculation means, so as to obtain at least one graphical or statistical value and/or at least one value characteristic of the grey levels for each plane, corresponding to a value characterizing the colour or of the tone of the skin; as well as to determine the luminosity value L, e) means for characterizing the tone of the skin or integuments on the basis of the combination of the value characterizing the colour of the skin or integuments and of the luminosity value L.

Figure 2:
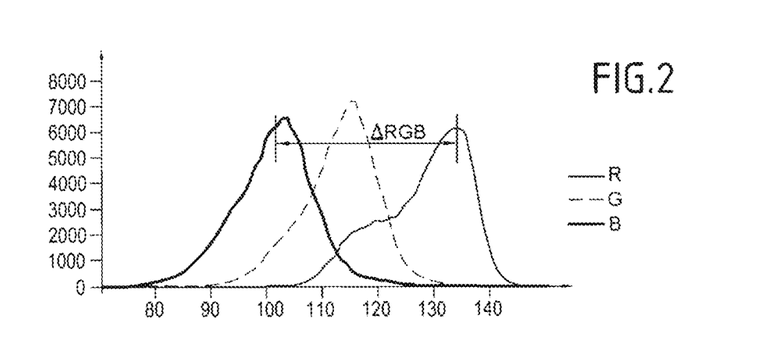
FIG. 2 represents an exemplary histogram R, G, B of the skin, taken in the zone of the brow, for each red, green or blue colour plane, in an orthonormal reference frame with here as horizontal axis or abscissa the set of values of grey levels of the pixels of the image, ordered from the darkest (on the left), to the lightest (on the right) and graded on a scale from 0 (pure black) to 255 (pure white); and as ordinate or as vertical axis, the number of pixels or else the proportion of these pixels in the image for each component R, G and B.

According to another particular embodiment of an invention, the apparatus is characterized in that the calculation means plot a histogram of each digital image in the form of a curve in a plane, and for which for example the vertical axis represents the number of pixels or the proportion of pixels in the image for each colour plane R, G and B and the horizontal axis represents the values of the grey levels of the pixels of the image, thereby obtaining a histogram R, a histogram G and a histogram B, as represented in FIG. 2.

A mathematical filter envisaged in the image analysis software can optionally be applied to each plane extracted from the image, so as to eliminate the spurious noise from the image, such as reflection.

According to a possible characteristic of the apparatus on the invention, said apparatus can comprise means of enlargement, for example an enlargement of four times, so as to magnify the details for example of the median zone of the brow 36, and/or of the median zone of the cheek 40, also integrated into said software of said image obtained by the camera allowing an operator to better visualize the skin imperfections and to evaluate the thresholding of the grey levels, making it possible to eliminate spurious elements or artefacts.

According to another advantageous characteristic of the apparatus according to the invention, said apparatus can comprise means for considering a thresholding of the grey levels, also integrated into the software, that is to say means making it possible to eliminate the grey levels that are below a certain predetermined grey level threshold, so as to eliminate spurious elements, thereby producing in this case an image ridded of spurious elements.

According to a particular embodiment of the apparatus according to the invention, said apparatus comprises means for recording, integrated into the software, at least one image or a plurality of images of the skin or integuments of one and the same person, in particular in several different zones, here the zones 36 of the brow and of each cheek 40, on a device for recording digital data integrated into the software.

According to another particular variant embodiment of the invention, the calculation means determine the colour characteristic of the skin or integuments by calculating the tightness either of the histograms R, G, B furthest apart, or of at least two of said histograms R, G, B denoted $\Delta_{RGB}$.

According to another particular variant embodiment of the invention, the apparatus is characterized in that the calculation means determine the desaturation of the image by calculating:

either the area of overlap of at least two histograms, preferably of the three histograms, R, G, B;

or the number of pixels for which a single value of the grid level is logged for the three planes R, G and B;

or the arithmetic mean and optionally the deviation from the mean, of said grid level logged for the three planes;

or else their combination(s).

According to another particular variant embodiment of the invention, the calculation means calculate a whiteness index ($I_w$) of the skin according to the formula:

$$(I_w) = \text{Arc} \tan(L/_{\Delta RGB})$$

According to a particular variant embodiment of the invention, the apparatus is characterized in that the calculation means calculate for each zone a value for the luminosity L, the index ($\Delta_{RGB}$) and the index ($I_w$) in particular for several selected zones of the skin or integuments.

According to another particular variant embodiment of the invention, the apparatus is characterized in that at least one selected zone of the skin or integuments exhibits a pigmentation defect such as a pigmentary blemish, and at least one other "control" skin zone is normally pigmented.

According to yet another particular variant embodiment of the invention, the apparatus is characterized in that it comprises means for extracting from said digital image 14, a limited area of the skin or integuments of the analysed person, on which the calculation means undertake the analysis of the colour and luminosity L over the whole of this limited area, and in particular the calculations of the parameters and the carrying out of the thresholding of the grey levels.

According to a particular variant, the limited area of the skin represents an area of about 1 cm² to 10 cm².

According to a particular variant embodiment of the invention, the apparatus is characterized in that it comprises a computer (50) combined with a monitor (52) comprising a screen (54), a keyboard (56) and a mouse (58) and comprising software, which may be off-the-shelf software for analysing digital images, integrating all of the abovementioned means including:

means for splitting the digital image into three colour planes Red, Green, Blue, termed R, G, B;

means for extracting each of these planes R, G, B;

means for calculating at least one of the following parameters on the basis of this plane;

the mean grey level of the image;

the area of the colour of the skin or integuments of said image;

the calculation of the luminosity L on the basis of the values of the grey levels of the three planes R, G, B;

the calculation of the hue angle ITA on the basis of the values of the grey levels of the three planes R, G, B;

the plot of the histograms of the image in each plane Red, Green, Blue, in the form of a two-dimensional curve for which the vertical axis represents the number of pixels or else the proportion of these pixels in the image for each component R, G and B, while the horizontal axis represents the set of values of grey levels of the pixels of the image, ordered from the darkest (on the left) to the lightest (on the right) and graded from a scale of 0 (pure black) to 225 (pure white) in accordance with FIG. 2.

The apparatus will also advantageously comprise the means for recording at least one image or a plurality of images of the skin or integuments.

According to another particular variant embodiment, the apparatus is characterized in that the calculation means take into account the mean of each parameter obtained in the various images, and obtained respectively with the various zones of the skin or integuments considered, of one or more people of a determined panel of people, so as to obtain each global mean parameter which is advantageously recorded, and can, according to a variant embodiment, be used for each person, to construct a curve for calibrating the tone of the skin.

Figure 3:
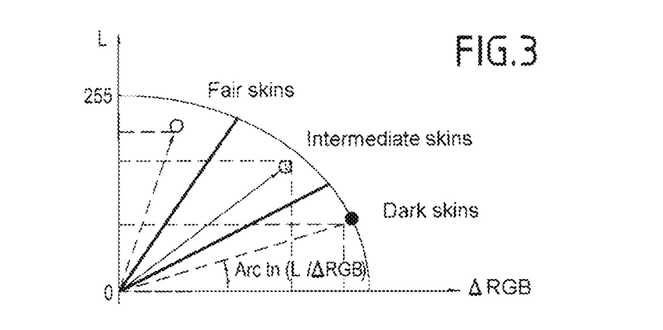
FIG. 3 represents as orthonormal reference frames the classification of the level here of natural whiteness of the skin or whiteness index, quantified by way of an "angle", given by the whiteness angle formula=Arc tn ($L/\Delta_{RGB}$), with as abscissa or as horizontal axis the value of $\Delta_{RGB}$ and as vertical axis or as ordinate the luminosity L thus showing a classification into dark skin, intermediate skin and fair skin.

These data can also be used to determine the tone of the skin and carry out a classification according to the orthonormal curve such as shown in FIG. 3.

It is understood that by virtue of the invention, the luminosity L close to that of mean grey is situated in the middle of the histogram represented in FIG. 2.

Moreover, the level of overlap of the three histograms R, G, B also constitutes the sign of a more or less considerable desaturation of the image.

Thus, the more similar the histograms are, the less saturated the image will be.

For example, white will be produced by the overlapping of the three curves R, G, B;

Yellow, magenta and cyan will appear when two of the curves R, G, B overlap;

Yellow will be produced by the superposition of curves R and G;

Magenta will be produced by the superposition of curves R and B;

And cyan will be produced by the superposition of curves G and B.

The overlap of the histograms can also be interpreted as a correlation with the HSL (Hue, Saturation, Lightness) system, which implies that a very bright, or very dark, hue cannot be strongly saturated.

The person skilled in the art understands from the foregoing that within the framework of the invention, starting from the combination of the histograms R, G, B and the luminosity L, it is possible to calculate an angle of whiteness making it possible to classify the levels of natural whiteness of the skin and/or its trend in the whiteness level of the skin subsequent to a cosmetic treatment with a whitening cosmetic product.

It will then be possible to quantify the whiteness level of the skin by way of an "angle", the formula for which is the following:

$$\text{whiteness angle} = \text{Arc} \tan(L/\Delta_{RGB});$$

A classification in the orthonormal axis as represented in FIG. 3 is thus obtained, making it possible to grade dark skins, intermediate skins and fair skins, as a function of the value of the whiteness angle.

Two examples of application of the apparatus of the method according to the invention such as previously described will now be described within the framework of an exemplary evaluation in terms of cosmetic efficacy of a cosmetic composition as regards make-up care on at least one person having need thereof.

EXAMPLE 2

Test for Evaluating the Cosmetic Efficacy of a Cosmetic Composition as Regards Care or Make-Up on a Person Having Need Thereof To evaluate the efficacy of a cosmetic care composition, use is made of an oil-in-water emulsion comprising active whitening agents.

This composition exhibits the following formula:

a) Whitening agents (% by weight)

| | |
|---|---|
| Ascorbyl glucoside | 2% |
| Aqueous solution of DNA sodium salt | 0.6% |
| Aqueous solution of extract of *Palmaria palmata* | 0.6% |

| | |
|---|---|
| Aqueous solution of extract of *Malva sylvestris* | 3% |
| Citric acid | 0.02% |

Cosmetically acceptable excipients of the emulsion qs 100%

To evaluate the efficacy of this cosmetic composition, one proceeds as follows:

a) At least one first colour digital image is captured before application of the cosmetic composition to at least one determined zone of skin or integuments with the aid of the camera 12;

b) The first digital colour image is decomposed into three colour planes R (red), G (green), B (blue) so as to determine the colour of the skin or integuments, as well as to determine the value of the luminosity L, as reference parameters of colour and luminosity L, of the skin or integuments before treatment;

c) The care or the make-up are undertaken, comprising one or more applications of said cosmetic composition to said at least one zone of skin or integuments over a predetermined time period;

d) At least one second digital image of said at least one zone of skin or integuments is captured, after said predetermined time period, and the current parameters of colour and luminosity L after treatment are determined, on said second image, as indicated under b);

e) The current parameters of colour and luminosity L of the second image obtained after treatment are compared with the reference colour and luminosity parameters L of the first image before treatment;

f) The efficacy or the absence of efficacy of said cosmetic composition is concluded as a function of the obtaining or of the non-obtaining of current parameters of colour and luminosity L that are significantly different from the reference parameters of colour and luminosity L.

According to a particular variant embodiment of the method, which is related also to the previous description of the apparatus and of the method for determining the tone of the skin, or of the integuments, the colour parameter is determined on each digital image decomposed into its three planes respectively of red colour, R; green colour, G; blue colour, B, termed R, G, B planes.

Thereafter, a histogram of each digital colour plane is plotted in the form of a curve in an orthonormal plane as indicated with reference to FIG. 2, thereby obtaining a green colour histogram, denoted G, a blue colour histogram, denoted B, and a red colour histogram, denoted R;

Moreover, it is advantageously possible to determine the mean colour value by calculating the level of overlap, of at least two histograms, preferably of the three histograms R, G, B, such as those represented in FIG. 2.

According to this method, it is also possible to determine the efficacy of the cosmetic composition by calculating the tightness, denoted $\Delta_{RGB}$, either of the histograms R, G, B furthest apart, or of at least two of said histograms R, G, B.

It is also possible to calculate a whiteness index ($I_w$) of the skin, according to the formula:

$$(I_w) = \text{Arc tan}(L/_{RGB}).$$

This whiteness index may be plotted as indicated with reference to FIG. 3.

Figure 4:
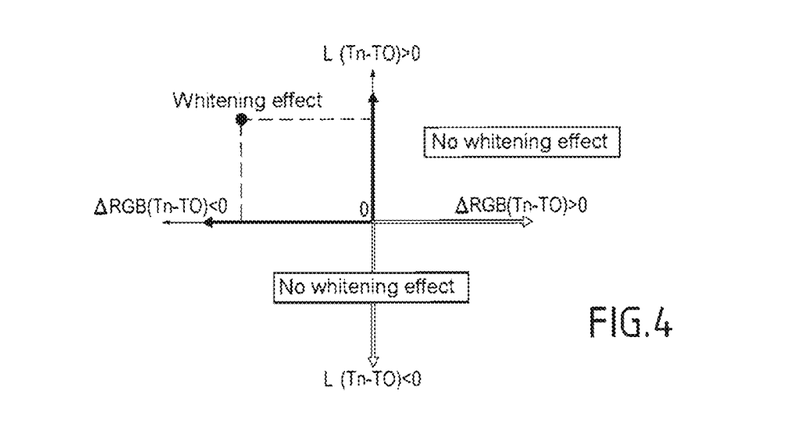
FIG. 4 represents the curves of trend in the whiteness level of the skin subsequent to the application of a cosmetic whitening composition, also in orthonormal reference frames. As abscissa or as horizontal axis is plotted the $\Delta_{RGB}$ (Tn−T0) or T0 is the instant T of starting of the application of the whitening cosmetic product and the instant Tn is the end day of application, corresponding to the $n^{th}$ day of the whitening cosmetic treatment. The vertical or ordinate axis represents the luminosity L in the form L (Tn-T0).

It is also possible to plot in orthonormal axes, the values of $\Delta_{RGB}$ and of L obtained between the treatment start day, denoted T0, and the $n^{th}$ day of treatment, denoted Tn, as represented in FIG. 4.

Generally, a whitening product will be considered to be efficacious if the values of L and $\Delta_{RGB}$, measured at T0 before treatment and at Tn after treatment, make it possible to describe a point whose coordinates lie within the space represented by the axes L (Tn −T0) greater than 0 and ΔRGB (Tn-T0) is less than zero, as represented in FIG. 4.

Moreover, a cosmetic product to be tested for its whitening effect will be considered to be efficacious if the trend in the whiteness angle Arc tan (L/($\Delta_{RGB}$)) between two determined time periods, for example at the time T0 before treatment and at the time Tn after a certain number of days of treatment, is positive.

In general, the application of the cosmetic composition is carried out over 8 weeks. The measurements may be taken at the time T0, at the time T=28 days (4 weeks); and at the time T=56 days (8 weeks).

EXAMPLE 3

Study of the Efficacy of a Cosmetic Product Such as that Described in Example 2, on a Total Panel of 40 Women Over 8 Weeks, Divided into Two Very Distinct Groups of Women Recruited According to their ITA-Based Complexion Within the framework of a larger-scale study of the efficacy of a cosmetic composition, such as that of example 2, in order to study its whitening efficacy, the grouping of two very distinct groups of women recruited according to their ITA-based complexion has been undertaken in China.

Thus, a panel of twenty women possessing a skin of medium to fair complexion, denoted group F, and a panel of twenty women possessing a complexion of fair to very fair, denoted group C, were recruited.

To carry out this classification, the individual typological angle ITA, which defines the degree of pigmentation of the skin, was measured. It will be noted that the lower the ITA, the more pigmented the skin. It is recalled that this angle ITA is obtained through the formula ITA=Arc tan (L−50): b*]×180: n.

Thus, at the various measurement times, start day 0 or T0 at 4 weeks or T4, and at 8 weeks or T8, a digital image of the three-quarter face is captured using the VISIA-CR apparatus distributed commercially by the company Canfield, with standard white light.

On these digital images captured according to the method described previously, the two parameters described previously, ΔRGB and L, were calculated by the calculation means.

In parallel, a clinical evaluation of the shade of the colour of the skin or of the entire face according to a validated graduation and a colorimetric measurement according to a CL400 colorimeter were performed.

Figure 5:
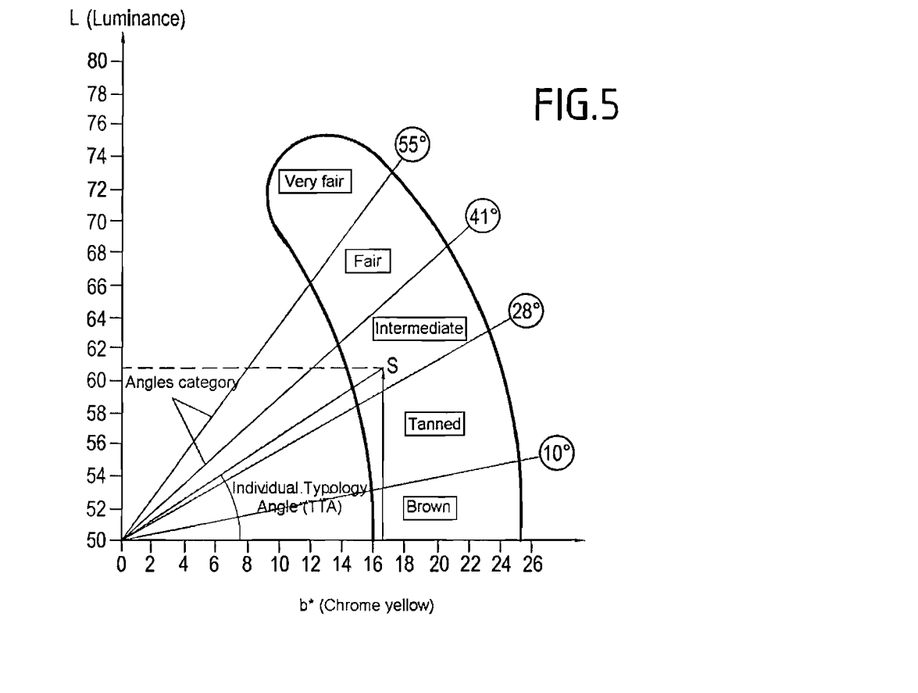
FIG. 5 represents the degree of complexion or of pigmentation of the skin established according to the individual typological angle ITA calculated according to the formula ITA=[Arc tan (L−50): b*]×180/n, with on the abscissa axis or horizontal axis, the values of b* (chrome yellow) according to a scale of values ranging from 0 to 26; and the ordinate axis or vertical axis represents the luminosity or luminance L on a scale ranging from 50 to 80.

An exemplary representation such as may stem from such a study is represented in FIG. 5.

It is observed that the measurement of the natural whitening of the skin by ΔRGB and L makes it possible to confirm the grading of the two groups of women.

The group of women having a skin of medium to fair complexion, denoted F in table I hereinbelow, possesses a lower whiteness angle than the group of women having a skin of fair to very fair complexion, denoted C in the table hereinbelow.

The classification of the two groups of women performed by $\Delta_{RGB}$ and L is also strongly correlated with that of the dermatologist and appears perfectly consistent with the colorimetric measurements (or hue angle ITA).

TABLE I

| | Whiteness angle | |
|---|---|---|
| Skin | | T0 |
| Very fair (C.) | | 55.3° |
| Fair (F.) | | 47.5° |

Figure 6:
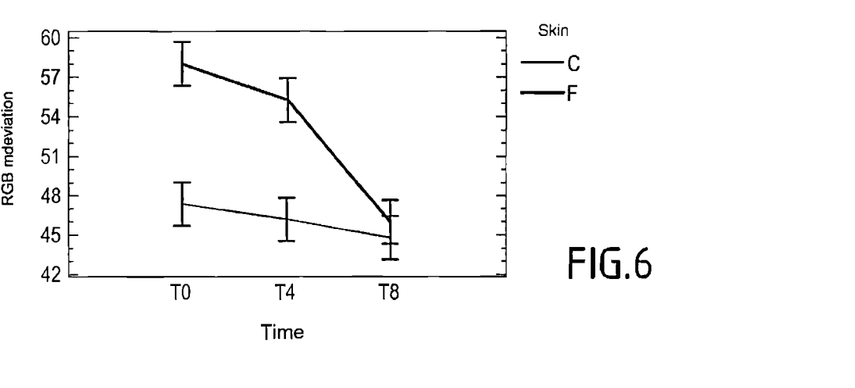
FIG. 6 represents the curves of trend in the deviation ΔRGB, as ordinate, and of the luminosity L, as abscissa, in the course of the cosmetic treatment, with a whitening cosmetic composition, of two groups of women graded into a group with skin of very fair to fair complexion, denoted C, and into a group with skin of medium to fair complexion F, showing here a significant decrease in the RGB deviations with in parallel an increase in the luminosity L, over the course of the treatment time at T4 (4 weeks) and at T8 (8 weeks).

The trend in the $\Delta_{RGB}$ and in the L in the course of the cosmetic treatment with the cosmetic composition of example 2, measured at time T=4 weeks and at time T=8 weeks, makes it possible to confirm for the two groups of women the whitening action of the tested product as is represented in FIG. 6.

The results are also listed in tables II, III, IV, V hereinafter.

TABLE II

| | Significance of the values of ΔRGB | | | |
|---|---|---|---|---|
| Skin | T0 | T4 | T8 | P FPS |
| Very fair (C.) | 47.1° | 45.9° | 44.4° | S × (T = 0.01) |
| Fair (F.) | 58.2° | 55.8° | 45.9° | S × (T = 0.01) |

TABLE III

| | Mean trend in the luminosity L* | | | |
|---|---|---|---|---|
| Skin | T0 | T4 | T8 | P FPS |
| Very fair (C.) | 67.8° | 68.6° | 68.7 | S × (T = 0.01) |
| Fair (F.) | 63.3° | 63.8° | 65.7 | S × (T = 0.01) |

TABLE IV

| | Mean trend in the whiteness angle | | | |
|---|---|---|---|---|
| Skin | T0 | T4 | T8 | P FPS |
| Very fair (C.) | 55.3° | 56.2° | 57.2° | S × (T = 0.01) |
| Fair (F.) | 45.4° | 48.8° | 55.1° | S × (T = 0.01) |

Index = Arc Tan (L*: ΔRGB)

TABLE V

| | Mean trend in the ITA hue angle | | | |
|---|---|---|---|---|
| Skin | T0 | T4 | T8 | P FPS |
| Very fair (C.) | 55.6° | 53.5° | 55.0° | S × (T = 0.01) |
| Fair (F.) | 37.4° | 40.6° | 48.2° | S × (T = 0.01) |

A significant decrease in the deviations R, G, B indicating a desaturation of the colour with, in parallel, an increase in the luminosity L may be observed on the basis of FIG. 6 and the tables II to V.

It is thus possible to retrieve this positive trend in the cosmetic treatment through the trend in the whiteness angle.

Thus, the whitening effect has been confirmed by the clinical evaluation and the measurement of the hue angle ITA.

The invention thus makes it possible to measure, safely and with high reproducibility, the efficacy or the non-efficacy of a cosmetic product. It is apparent to the person skilled in the art that the invention is not limited to the measurement of the whitening effect of a cosmetic product.

The invention can also find application to tanning care by application of a cosmetic tanning composition for a predetermined period of time, making it possible to conclude as to the efficacy or the absence of efficacy of tanning of the cosmetic composition as a function of the obtaining or of the non-obtaining of current parameters of colour and luminosity L.

It is thus understood that the invention may be implemented according to diverse variants without departing from the scope thereof.

The invention also covers all the means constituting technical equivalents of the means described as well as their diverse combinations.

What is claimed is:

1. A method for characterizing the tone of the skin or integuments of a person, comprising the following steps:
   a) capturing at least one digital colour image of at least one determined zone of skin or of integuments, said image being defined by a multiplicity (N) of pixels, each pixel having a grey level, with the aid of a digital camera or a digital photographic apparatus, and transmitting said digital colour image to a digital image processing device for processing and recording said at least one digital image therein;
   b) splitting the digital colour image thus recorded into three colour planes: a red plane R, a green plane G, and a blue plane B, with said digital image processing device;
   c) extracting each of these planes R, G, B; and calculating and logging, with said digital processing device, on each plane the grey level value for each of the N pixels, thereby providing N grey level values, which are processed mathematically by mathematical calculation means, to obtain at least one value selected from a graphical grey value, a statistical grey value, and at least one average grey value characteristic of the grey levels for each plane, corresponding to a grey value characterizing the colour of the skin;
   d) plotting a histogram of each plane R, Plane G, and plane B from the digital image in the form of a curve in a plane, and for which the vertical axis represents the number of pixels or the proportion of pixels in the image for each colour plane R, G, and B, and the horizontal axis represents the values of the grey levels of the pixels of the image, or vice versa, thereby obtaining respectively a histogram R, a histogram G, and a histogram B, said method, including determining the colour characteristic of the skin or integuments by calculating the tightness, denoted ($\Delta_{RGB}$), of the histograms R, G, B furthest apart and calculating a whiteness index ($I_w$) of the skin according to the formula:

$(I_w)$=Arc tn$(L/\Delta_{RGB})$, where $L$ is Luminosity;

e) evaluating the Luminosity L from the value of the grey level resulting from at least some of the N pixels of the image for each colour plane of at least two colour planes of the three colour planes R, G, B; and
   f) characterizing the tone of the skin or integuments from both the combination of the value characterizing the colour of the skin or integuments and of the Luminosity value L.

2. The method of claim 1, comprising selecting an image zone representative of the tone to be observed and calculating on at least one part of this zone, at least one parameter selected from the mean grey level of the image, the aggregate surface area of the grey levels, and the grey level variance.

3. The method according to claim 1, comprising determining the more or less saturated/desaturated character of a mean colour, or of a saturation of a mean colour, by calculating from said calculation means:

either the area of overlap of at least two histograms from the three histograms R, G, B, or the number of pixels for which a single grey level value is logged for the three planes R, G and B, or the arithmic mean and optionally the deviation from the mean, of the grey levels logged for the three planes, or any of their combinations.

4. The method of claim 1, comprising reproducing said steps a) to f) on various skin zones of the face of the same individual.

5. The method of claim 4, comprising calculating a value for the luminosity L, the index ($\Delta_{RGB}$) and the index ($I_w$) for each zone.

6. The method of claim 1, comprising selecting at least one skin zone exhibiting a pigmentation defect including a pigmentary blemish, and at least one other control skin zone naturally pigmented.

7. The method of claim 1, comprising performing said image capture of said at least zone of the skin under illumination with white light.

8. The method of claim 1, comprising using a digital colour camera selected from a CCD digital camera and a CMOS digital photographic apparatus.

9. The method of claim 1, wherein the calculation means take into account the mean of each parameter obtained on the various images obtained respectively with the various zones of the face or of the integuments considered, thereby obtaining each global mean parameter of the face which is recorded and is used, for each person, to construct a curve for calibrating the tone of the skin or integuments.

10. The method of claim 1, comprising:
a) using the colour of the skin or integuments, and the value of the luminosity L determined from said at least one image, named first image, as reference parameters of colour and luminosity L of the skin or integuments before a care or make-up with a cosmetic composition;
b) undertaking the care or make-up, comprising one or more applications of said cosmetic composition to said at least one zone of skin or integuments over a predetermined period of time;
c) capturing at least one second digital image of said at least one zone of skin or integuments, after said predetermined period of time, and determining the current parameters of colour and luminosity L after treatment as indicated under b), on said second image;
d) comparing the current parameters of colour and luminosity L of the second image obtained after treatment with the reference parameters of colour and luminosity L of the first image before treatment; and
e) concluding the efficacy or the absence of efficacy of said cosmetic composition as a function of the obtaining or of the non-obtaining of current parameters of colour and luminosity L that are significantly different from the reference parameters of colour and luminosity L.

11. The method of claim 10, comprising determining the colour parameter on each split digital image into three colour planes respectively a Red plane, R; a Green plane, G; and a Blue plane, B.

12. The method of claim 10, comprising determining a mean colour value by calculating the level of overlap of at least two histograms of the three histograms R, G, B.

13. The method of claim 10, comprising determining the efficacy of the cosmetic composition by calculating the tightness, denoted ($\Delta_{RGB}$), of the histograms R, G, B furthest apart.

14. The method of claim 10, comprising determining the efficacy of the cosmetic composition by calculating the tightness, denoted ($\Delta_{RGB}$) of at least two histograms of said histograms R, G, B.

15. The method of claim 10, comprising reproducing said method on various skin zones of the same individual.

16. The method of claim 15, comprising calculating a value for the luminosity L, the index ($\Delta_{RGB}$) and the index ($I_w$) for each zone.

17. The method of claim 10, comprising selecting at least one zone of skin or integuments exhibits a pigmentation defect including pigmentary blemish, and at least one other control skin zone naturally pigmented.

18. The method of claim 10, comprising performing a whitening care on said at least one zone of skin or integuments, and applying a cosmetic whitening composition during said predetermined period of time, to conclude as to the efficacy, or the absence of efficacy, of whitening, of said cosmetic composition as a function of the obtaining, or of the non-obtaining, of current parameters of colour and luminosity L that are significantly different from the reference parameters of colour and luminosity L.

19. The method of claim 18, comprising calculating the whiteness index and concluding as to the efficacy, or the non-efficacy, of the cosmetic composition depending on whether the trend in the whiteness index is or is not significantly positive.

20. The method of claim 10, comprising performing a tanning on said at least one zone of skin or integuments, said tanning comprising applying a cosmetic tanning composition, during said predetermined period of time, to conclude as to the efficacy, or the absence of efficacy, of tanning, of said cosmetic composition as a function of the obtaining, or of the non-obtaining, of current parameters of colour and luminosity L that are significantly different from the reference parameters of colour and luminosity L.

21. The method of claim 10, wherein the significant difference is obtained when a probability of error is of less than or equal to 5%.

22. The method of claim 10, comprising performing said evaluating of cosmetic efficacy on a panel of people of a group representative of a given age category, to determine the significant character of efficacy of the cosmetic product considered.

23. The method of claim 22, comprising selecting said group of people according to their skin colour representative of their index or Individual Typological Angle, rated respectively as very fair skin, fair skin, medium skin and dividing them into two panels, a first panel ranging from very fair skin to fair skin, and a second panel ranging from fair skin to medium skin;
performing the steps a) to e) mentioned in claim 10 on each person of each panel, and
concluding the positive or negative efficacy of the cosmetic composition considered when a similarly evolving trend is found in the 2 panels.

* * * * *